(12) United States Patent
Hayashi et al.

(10) Patent No.: US 11,092,535 B2
(45) Date of Patent: Aug. 17, 2021

(54) IMAGING TARGET ANALYSIS DEVICE, FLOW CHANNEL STRUCTURE, IMAGING MEMBER, IMAGING METHOD, AND IMAGING TARGET ANALYSIS SYSTEM

(71) Applicant: Sony Corporation, Tokyo (JP)

(72) Inventors: Nobuhiro Hayashi, Kanagawa (JP); Yuichi Mizutani, Saitama (JP); Kiyoshi Osato, Chiba (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 16/606,823

(22) PCT Filed: Feb. 6, 2018

(86) PCT No.: PCT/JP2018/003974
§ 371 (c)(1),
(2) Date: Oct. 21, 2019

(87) PCT Pub. No.: WO2018/198470
PCT Pub. Date: Nov. 1, 2018

(65) Prior Publication Data
US 2020/0049613 A1    Feb. 13, 2020

(30) Foreign Application Priority Data
Apr. 28, 2017    (JP) .............................. JP2017-090665

(51) Int. Cl.
*G01N 15/14*    (2006.01)
*G01N 33/493*    (2006.01)
(Continued)

(52) U.S. Cl.
CPC ..... *G01N 15/1425* (2013.01); *G01N 15/1434* (2013.01); *G01N 33/493* (2013.01);
(Continued)

(58) Field of Classification Search
CPC .......... G01N 15/1425; G01N 15/1434; G01N 15/147; G01N 15/1475; G01N 2015/1006;
(Continued)

(56) References Cited

U.S. PATENT DOCUMENTS

| | | |
|---|---|---|
| 5,880,835 A | 3/1999 | Yamazaki et al. |
| 2003/0017076 A1* | 1/2003 | Kochy ............... G01N 15/1459 422/81 |

(Continued)

FOREIGN PATENT DOCUMENTS

| | | |
|---|---|---|
| EP | 0556971 A1 | 8/1993 |
| JP | 62-228139 A | 10/1987 |

(Continued)

OTHER PUBLICATIONS

International Search Report and English translation thereof dated Apr. 24, 2018 in connection with International Application No. PCT/JP2018/003974.

*Primary Examiner* — Joon Kwon
(74) *Attorney, Agent, or Firm* — Wolf, Greenfield & Sacks, P.C.

(57) ABSTRACT

To provide a technology for increasing the speed of sample imaging using a microscope.
The present technology provides a flow channel structure including an imaging flow channel in which a fluid containing imaging targets flows in the same direction as the optical axis of an objective lens. The present technology also provides an imaging member including the flow channel structure. The present technology also provides an imaging method that includes imaging an imaging target in an imaging flow channel in which a fluid containing the imaging target flows in the same direction as the optical axis of an objective lens. The present technology also provides an (Continued)

imaging target analysis device and an imaging target analysis system that include the imaging member.

16 Claims, 9 Drawing Sheets

(51) Int. Cl.
*G02B 21/36* (2006.01)
*G06T 7/70* (2017.01)
(52) U.S. Cl.
CPC .............. *G02B 21/367* (2013.01); *G06T 7/70* (2017.01); *G06T 2207/10056* (2013.01)
(58) Field of Classification Search
CPC ..... G01N 2015/144; G01N 2015/1445; G01N 33/493; G02B 21/367; G06T 2207/10056; G06T 7/70
See application file for complete search history.

(56) References Cited

U.S. PATENT DOCUMENTS

| | | | |
|---|---|---|---|
| 2010/0220312 A1* | 9/2010 | Iwai | G01N 15/1434 356/39 |
| 2013/0129578 A1* | 5/2013 | Jeong | B01L 3/502761 422/255 |
| 2013/0177973 A1 | 7/2013 | Kondo | |
| 2017/0333903 A1* | 11/2017 | Masaeli | B01L 3/502761 |
| 2018/0321128 A1* | 11/2018 | Harriman | G01N 15/1434 |

FOREIGN PATENT DOCUMENTS

| | | |
|---|---|---|
| JP | 05-296915 A | 11/1993 |
| JP | 08-320285 A | 12/1996 |
| JP | 2002-071549 A | 3/2002 |
| JP | 2004-069431 A | 3/2004 |
| JP | 2004-150942 A | 5/2004 |
| JP | 2013-015357 A | 1/2013 |
| WO | WO 2008/007725 A1 | 1/2008 |
| WO | WO 2008/007725 A1 | 12/2009 |

\* cited by examiner

IMAGING TARGET ANALYSIS DEVICE, FLOW CHANNEL STRUCTURE, IMAGING MEMBER, IMAGING METHOD, AND IMAGING TARGET ANALYSIS SYSTEM

CROSS-REFERENCE TO RELATED APPLICATIONS

This application claims the benefit under 35 U.S.C. § 371 as a U.S. National Stage Entry of International Application No. PCT/JP2018/003974, filed in the Japanese Patent Office as a Receiving Office on Feb. 6, 2018, which claims priority to Japanese Patent Application Number JP2017-090665, filed in the Japanese Patent Office on Apr. 28, 2017, each of which is hereby incorporated by reference in its entirety.

TECHNICAL FIELD

The present technology relates to an imaging target analysis device, a flow channel structure, an imaging member, an imaging method, and an imaging target analysis system. More particularly, the present technology relates to a method of imaging an imaging target in a fluid, a flow channel structure to be used for imaging an imaging target in a fluid, an imaging member including the flow channel structure, and a device and a system to be used for analyzing an imaging target in a fluid.

BACKGROUND ART

In a case where a test result is positive in a health checkup or in a urine check such as a uric protein test or a uric occult blood test in a complete medical checkup, a urine sediment test is conducted on a sediment obtained by centrifuging urine. The urine sediment test is conducted to check the type, the number, and/or the amount of solid components such as red blood cells, white blood cells, uric acid crystals, cells, and bacteria, for example.

In a case where the numerical value relating to the solid components is higher than a normal value, or abnormal cells such as columnar cells are observed as a result of the urine sediment test, a disease in the urinary tract or the kidney is suspected, for example. The result of the urine sediment test is also useful as information for making a decision in diagnosing various diseases in the entire body. In a case where an abnormal value is detected in the urine sediment test, a secondary test such as a renal function test or a urinary tract X-ray test or an imaging test is further conducted.

The urine sediment test is conducted by a flow cytometry technique or a microscopic examination technique, for example.

By the flow cytometry technique, urine is irradiated with laser light, and the light generated by the irradiation is then analyzed, so that the solid components in the urine are automatically quantified. The flow cytometry technique is useful as a screening test. However, the solid components that can be analyzed by the flow cytometry technique are limited. Furthermore, morphological information about the solid components is obtained by the flow cytometry technique. Therefore, a test with a microscope (the microscopic examination technique) is also used, to conduct more detailed analysis.

By the microscopic examination technique, the sediment obtained by centrifuging urine is placed on a slide glass, the sediment is covered with a cover glass, and morphological information about the solid components in the sediment is observed with a microscope. For example, in a case where zero to four red blood cells, zero to four white blood cells, and a small amount of other epithelial cells and crystals are observed in one field of view, the state may be determined to be normal.

A urinary tangible component analyzer has been suggested and put into practical use, to automate microscopic examination. For example, Patent Document 1 listed below discloses a "device for analyzing tangible components contained in a sample held between a light transmission plate and a coated light transmission plate" (claim 1). The device includes: "an objective lens for observing the sample; a focusing detection means that detects a focused state of the objective lens; a driving means that changes the relative positions of the objective lens and the sample in a three-dimensional direction; an automatic focusing means that automatically adjusts the focal point of the objective lens by controlling the driving means, on the basis of a result of the detection performed by the focusing detection means; a control means that controls the automatic focusing means and/or the driving means to perform an automatic focusing operation from a predetermined analysis start position to a predetermined analysis end position between the light transmission plate and the coated light transmission plate; and a determination means that determines that there exist tangible components at a focused position in a case where the focused state is detected by the focusing detection means" (claim 1). An example of such a device put into practical use is USCANNER (registered trademark) (E) (Toyobo Co., Ltd.).

CITATION LIST

Patent Document

Patent Document 1: WO 2008/007725 A

SUMMARY OF THE INVENTION

Problems to be Solved by the Invention

In a conventional test using a microscope, the three-dimensional structure of the object is recognized, and the object is observed while the focus is adjusted. However, in a case where a certain focus plane is selected in imaging, it is not possible to obtain image data in each case where the focus position is changed. To obtain image data in each case where the focus position is changed, it is necessary to increase the number of images to be captured in imaging. Performing imaging at each focus position will lead to an increase in the time required for imaging.

Further, in acquiring digital images of a sample with a microscope, imaging in a plurality of fields of view and a plurality of focus positions is normally performed according to the workflow described below. In the workflow described below, the X direction, the Y direction, and the Z direction are moving directions of a stage that holds a slide glass on which an imaging target is placed. The X direction and the Y direction are directions perpendicular to the optical axis of an objective lens, and the X direction and the Y direction are perpendicular to each other. The Z direction is the optical axis direction of the objective lens.

1. The stage is moved in the X direction and the Y direction, and the desired field of view in which imaging is to be performed is selected.

2. The stage is moved in the Z direction as needed, and the focus is adjusted.

3. A digital image is obtained by imaging.

4. The above steps 2 and 3 are repeated, so that a plurality of images with varied focal points in the selected field of view is obtained.

5. The above steps 1 through 4 are repeated, so that images in a plurality of desired fields of view are obtained.

In this workflow, the above step 1 of moving the stage in the X direction and the Y direction requires mechanical movement, and therefore, requires time. Further, the above focus adjustment step 2 does not take a longer time than the above step 1 in a case where any mechanical movement of the stage is not involved. However, the focus adjustment step 2 still requires time. Furthermore, in a case where the number of images to be obtained in the above step 4 becomes larger, the time required for the focus adjustment step 2 becomes longer accordingly.

If a higher-speed sensor is used for capturing digital images, an increase in the speed of the processing in the above step 3 can be expected. However, the above steps 1 and 2 involving mechanical movement are time consuming, and therefore, the entire process for acquiring digital images of a sample with a microscope takes a long time.

The present technology aims to increase the speed of sample imaging using a microscope.

Solutions to Problems

The present inventors have found that the above problems can be solved with the use of a specific flow channel structure.

Specifically, the present technology provides a flow channel structure including an imaging flow channel in which a fluid containing an imaging target flows in the same direction as the optical axis of an objective lens.

In one embodiment of the present technology, the flow channel structure may include at least one fluid introduction channel that introduces the fluid into the imaging flow channel.

In one embodiment of the present technology, the direction of the fluid introduction channel may differ from the direction of the imaging flow channel.

In one embodiment of the present technology, the flow channel structure may include at least two of the fluid introduction channels, and the at least two fluid introduction channels may merge on the optical axis.

In one embodiment of the present technology, the flow channel structure may include at least one fluid ejection channel that ejects the fluid having passed through the imaging flow channel to the outside of the flow channel structure.

In one embodiment of the present technology, the direction of the fluid ejection channel may differ from the direction of the imaging flow channel.

In one embodiment of the present technology, the flow channel structure may include at least two of the fluid ejection channels, and the at least two fluid ejection channels may branch from the imaging flow channel.

In one embodiment of the present technology, the fluid may be a liquid.

In one embodiment of the present technology, the fluid may be a liquid obtained from a living organism.

In one embodiment of the present technology, the fluid may be urine or a urine-derived liquid.

In one embodiment of the present technology, the flow channel structure may include a vibrator.

The present technology also provides an imaging member including the flow channel structure.

The present technology also provides an imaging method that includes imaging an imaging target in an imaging flow channel in which a fluid containing the imaging target flows in the same direction as the optical axis of an objective lens.

In one embodiment of the present technology, the imaging may be performed in a state in which the position of the imaging flow channel is fixed with respect to the objective lens.

In one embodiment of the present technology, the imaging may be performed a plurality of times.

In one embodiment of the present technology, the frame rate in the imaging performed the plurality of times may be equal to or higher than the numerical value of the quotient obtained by dividing the flow velocity of the fluid in the region to which the focal point is adjusted in the imaging by the depth of field.

In one embodiment of the present technology, the method may further include obtaining an image relating to the three-dimensional shape of the imaging target, on the basis of image data obtained through the imaging performed the plurality of times.

The present technology also provides an imaging target analysis device that includes: an imaging member including a flow channel structure including an imaging flow channel in which a fluid containing an imaging target flows in the same direction as the optical axis of an objective lens; and an imaging unit that performs imaging of the imaging target through the objective lens.

In one embodiment of the present technology, the imaging member may be replaceable.

In one embodiment of the present technology, the area of a cross-section of the imaging flow channel may be larger than the area of the field of view of the objective lens.

The present technology also provides an imaging target analysis system that includes: an imaging member including a flow channel structure including an imaging flow channel in which a fluid containing an imaging target flows in the same direction as the optical axis of an objective lens; and an imaging unit that performs imaging of the imaging target through the objective lens.

Effects of the Invention

According to the present technology, it is possible to increase the speed of sample imaging using a microscope. Note that the effects to be achieved by the present technology are not limited to the effect described herein, and may include any of the effects described in the present disclosure.

MODES FOR CARRYING OUT THE INVENTION

The following is a description of preferred embodiments for carrying out the present technology. Note that the embodiments described below are typical embodiments of the present technology, and do not narrow the interpretation of the scope of the present technology. Note that explanation will be made in the following order.

1. Description of a conventional technology
2. Basic concept of the present technology
3. First embodiment (a flow channel structure and an imaging member)
   (1) Description of the first embodiment
   (2) First example (a flow channel structure) of the first embodiment
   (3) Second example (a flow channel structure) of the first embodiment
   (4) Third example (a flow channel structure) of the first embodiment
   (5) Fourth example (a flow channel structure) of the first embodiment
   (6) Fifth example (a flow channel chip) of the first embodiment
   (7) Sixth example (a flow channel chip) of the first embodiment
4. Second embodiment (an imaging method)
   (1) Description of the second embodiment
   (2) First example (an imaging method) of the second embodiment
   (3) Second example (an imaging method) of the second embodiment
5. Third embodiment (an imaging target analysis device)
   (1) Description of the third embodiment
   (2) Example of the third embodiment (an imaging target analysis device)
6. Fourth embodiment (an imaging target analysis system)
   (1) Description of the fourth embodiment
   (2) Example of the fourth embodiment (an imaging target analysis system)

1. Description of a Conventional Technology

Figure 1:
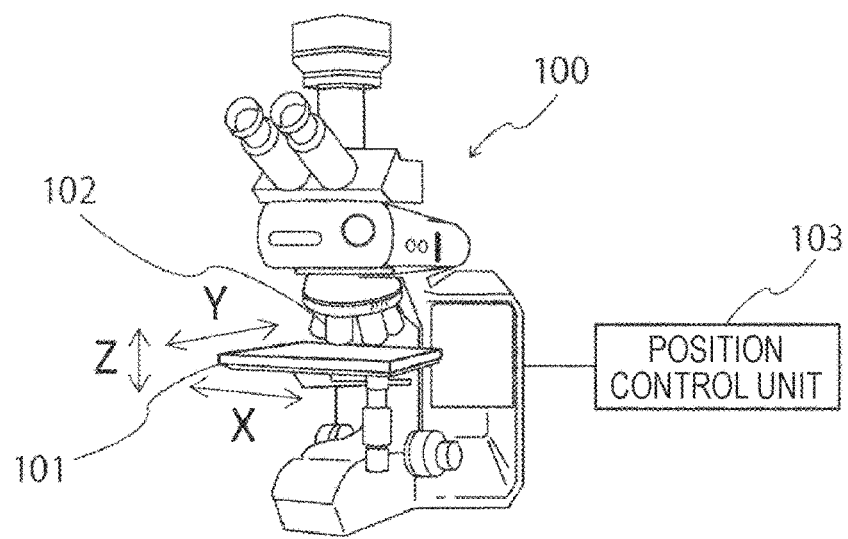
FIG. 1 is a diagram showing the moving directions of a stage of a microscope.

Referring now to FIG. 1, a conventional technology relating to sample imaging using a microscope is described below.

FIG. 1 is a diagram showing the moving directions of a stage 101 of a microscope 100. As shown in FIG. 1, the X direction, the Y direction, and the Z direction are the moving directions of the stage 101 on which the sample to be observed is placed. The X direction and the Y direction are directions perpendicular to the optical axis of an objective lens 102, and the X direction and the Y direction are perpendicular to each other. The Z direction is the optical axis direction of the objective lens 102. The stage 101 on which the sample to be observed is placed is moved to a desired position by a stage position control unit 103 connected to the microscope 100.

The stage position control unit 103 first moves the stage 101 in the X direction and/or the Y direction, to move a certain field of view into the field of view of the objective lens. The stage position control unit 103 then moves the stage 101 in the Z direction, to move the sample to a certain focus position. An image of the sample is then captured by a digital camera through the microscope at the focus position, so that a digital image of the sample is obtained. The stage position control unit 103 then moves the stage 101 in the Z direction, to move the sample to another focus position. An image of the sample is then captured by the digital camera through the microscope at the focus position, so that a digital image is obtained. As the above process is repeated a plurality of times, digital images of the sample at a plurality of focus positions in the certain field of view are obtained.

Next, the stage position control device 103 then moves the stage in the X direction and/or the Y direction, to move another field of view into the field of view of the objective lens. Digital images of the sample at a plurality of focus positions are then obtained also for this field of view in the above described manner.

To obtain a plurality of digital images of a sample as described above, it is necessary to mechanically move the stage 101, which takes time.

2. Basic Concept of the Present Technology

Figure 2:
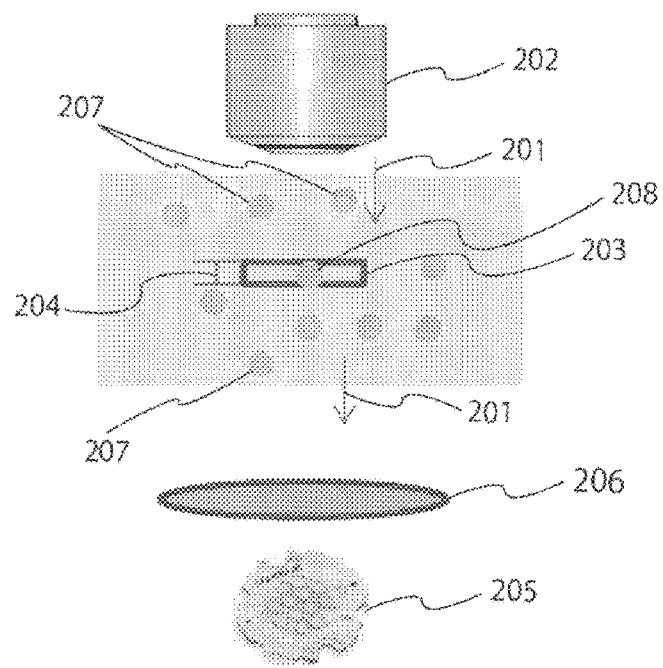
FIG. 2 is a diagram showing the basic concept of the present technology.

FIG. 2 shows the basic concept of the present technology. In FIG. 2, an arrow 201 indicates the direction of flow of a fluid. The field of view and the focal point of an objective lens 202 are adjusted to a region 203. The depth of field of the objective lens is a distance 204 in the optical axis direction. Light is emitted from a light source 205 toward imaging targets 207 through an illumination optical system 206. In the present technology, the imaging targets 207 are made to flow in the same direction as the optical axis of the objective lens. Of the flowing imaging targets, the imaging targets existing within the region 203 at the time of imaging are imaged through the objective lens 202. In a case where imaging is performed in the state shown in FIG. 2, an image of the imaging target 208 passing through the region 203 is captured. In the present technology, the focal point of the objective lens 202 may be fixed to the region 203.

In the present technology, it is not necessary to move the field of view in the X direction and/or the Y direction as described above in "1. Description of a conventional technology". As imaging is performed a plurality of times according to the present technology, it is possible to obtain image information that is similar to that to be obtained when imaging is performed in a plurality of fields of view, without moving the field of view of the objective lens.

Further, in the present technology, there is no need to adjust the focal point to an imaging target by operating the objective lens as described above in "1. Description of a conventional technology". In the present technology, after the focal point is adjusted to the region 203, it is possible to capture images of the imaging targets, without carrying out a step of adjusting the focal point of the objective lens.

Figure 3:
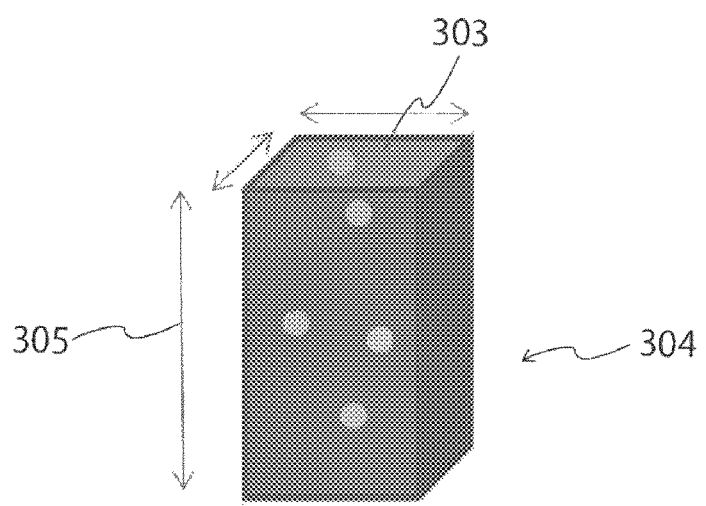
FIG. 3 is a conceptual diagram of stereoscopic image data obtained by processing image data so that images obtained by performing imaging a plurality of times in a successive manner are superimposed on one another.

Furthermore, the imaging may be performed the plurality of times in a successive manner. As image data is processed so that the images obtained through the imaging performed successively the plurality of times are superimposed on one another, stereoscopic image data shown in FIG. 3 is obtained, for example. FIG. 3 is a conceptual diagram of stereoscopic image data 304 obtained by superimposing image data obtained by performing imaging a plurality of times in a field of view 303. In FIG. 3, the direction indicated by an arrow 305 is the direction in which images are superimposed on one another. It becomes possible to more accurately observe the three-dimensional shape of each imaging target, on the basis of such stereoscopic image data. It also becomes possible to determine the number of imaging targets existing in a sample with a predetermined volume.

3. First Embodiment (Flow Channel Structure and Imaging Member)

(1) Description of the First Embodiment

The present technology provides a flow channel structure including an imaging flow channel in which a fluid containing imaging targets flows in the same direction as the optical axis of an objective lens. In the present technology, the focal point of an objective lens is adjusted to a certain region in the imaging flow channel. When imaging is performed through the objective lens, an image of each imaging target present in the region is captured. In a case where the flow channel structure of the present technology is used for imaging imaging targets, the fluid containing the imaging targets flows in the imaging flow channel in the same direction as the optical axis of the objective lens. After the focal point is adjusted to the predetermined region, it is not necessary to carry out the step of adjusting the focal point to an imaging target by operating the objective lens.

In the present technology, the imaging flow channel refers to a flow channel including the region to which the focal point of the objective lens to be used for imaging according to the present technology is adjusted. As imaging is performed through the objective lens, images or image data of solid objects present in the region is obtained. In the present technology, imaging is performed through an objective lens. The imaging may be performed by an imaging device such as a digital camera provided in a microscope such as an optical microscope, for example.

The region may be defined by the field of view and the depth of field of the objective lens. For example, in a case where the field of view is circular, the region may be a cylindrical region whose height is equal to the depth of field.

The field of view of the objective lens may be appropriately selected by a person skilled in the art. For example, the field of view of the objective lens may be selected so as to cover any range of a cross-section in the imaging flow channel, or may be selected so as to cover an entire cross-section in the imaging flow channel.

The depth of field may be appropriately selected by a person skilled in the art. For example, it is possible to select a desired depth of field by selecting a type of objective lens.

In the present technology, the optical axis of the objective lens is the straight line passing through the center and the focal point of the objective lens. In the present technology, the fluid containing the imaging targets is only required to flow in the same direction as the optical axis of the objective lens in at least part of the imaging flow channel. For example, in the imaging channel, the fluid containing the imaging targets flows in the same direction as the optical axis of the objective lens only in the central portion in the imaging flow channel, and the fluid containing the imaging targets flows in a different direction from the optical axis of the objective lens in a portion near the wall surface of the imaging flow channel.

Further, in the present technology, the fluid containing the imaging targets may flow from the light source toward the objective lens or from the objective lens toward the light source in the imaging flow channel. The flow channel structure of the present technology may be designed so that the direction of the imaging flow channel is the direction of action of gravity or the direction of action, or may be designed so that the direction of the imaging flow channel is a horizontal direction or an oblique direction with respect to the direction of action of gravity.

In the present technology, the fluid may be any fluid that can be moved so that the imaging targets flow. For example, the fluid may be a liquid substance, or more particularly, a liquid, or a gaseous substance, or more particularly, a gas. Alternatively, the fluid may be a vacuum. Examples of the liquid substance include, but are not limited to, liquids obtained from living organisms, beverages, liquid foods, liquids containing microorganisms, and liquids containing particles. Examples of liquids obtained from living organisms include, but are not limited to, urine and urine-derived fluids, blood and blood-derived liquids such as plasma and serum, lymph fluids and liquids derived from lymph fluids, and dilutions and concentrates of these liquids.

The amount of the fluid made to flow in the imaging flow channel in one imaging process using the flow channel structure of the present technology is 0.1 μl to 10 ml, or particularly, 0.2 μl to 1 ml, or more particularly, 0.3 μl to 500 μl, or even more particularly, 0.5 μl to 100 μl, or yet more particularly, 1 μl to 50 μl, for example. For example, in a common microscopic examination of urine, a sample obtained by concentrating about 4.5 μl of urine is subjected to microscopic observation. The amount of urine may be applied, without being concentrated, in a single imaging process using the flow channel structure of the present technology. Through the imaging process, it becomes possible to obtain images of solid components in urine and/or analyze the solid components in the urine in a shorter time than in conventional cases.

In the present technology, an imaging target may be a solid object that can flow in the flow channel while being contained in a fluid, and an image of the solid object can be captured by imaging performed through an objective lens.

In the present technology, imaging targets may be particles that can be observed with a microscope, for example. Examples of such particles include, but are not limited to, biological microparticles such as cells, microorganisms, solid components derived from living organisms, and liposomes, and synthetic particles such as latex particles, gel particles, and industrial particles. Further, examples of the particles include microparticulate substances to be used as an indicator of air pollution, such as PM 2.5.

Examples of the cells include animal cells (such as cells contained in urine and blood cells) and plant cells. Examples of the solid components derived from living organisms include crystals produced in living organisms. Examples of the microorganisms include bacteria such as Escherichia coli, and fungi such as yeast. The synthetic particles may be particles formed with an organic or inorganic polymeric material, or a metal, for example. Examples of the organic polymeric material include polystyrene, styrene divinyl benzene, and polymethyl methacrylate. Examples of the inorganic polymeric material include glass, silica, and magnetic materials. Examples of the metal include gold colloids and aluminum.

In the present technology, preferred examples of imaging targets include, but are not limited to, solid components derived from living organisms, and microorganisms. Examples of the solid components derived from living organisms include cells and crystals derived from living organisms. In a case where the fluid to be subjected to imaging is urine or a liquid derived from urine, the imaging targets may be of at least one type of the following cells and the like: red blood cells, white blood cells, other cells such as epithelial cells and columnar cells, crystals, and bacteria, for example. Examples of the crystals include calcium oxalate crystals, uric acid crystals, calcium phosphate crystals, ammonium magnesium phosphate crystals, ammonium urate crystals, sodium urate crystals, calcium carbonate crystals, bilirubin crystals, tyrosine crystals, leucine crystals, cholesterol crystals, cystine crystals, and 2,8-dihydroxyadenine crystals (DHA crystals).

In the present technology, the shape of a cross-section of the flow channel forming the flow channel structure of the present technology may be appropriately determined by a person skilled in the art. The shape of a cross-section of the flow channel may be a rectangular shape, a square shape, a circular shape, a semicircular shape, an elliptical shape, a semielliptical shape, or a trapezoidal shape, for example, but is not necessarily one of these shapes. In preferred embodiments of the present technology, the cross-sectional shape of the flow channel may be a rectangular shape, a square shape, a circular shape, or an elliptical shape. Note that circular shapes include substantially circular shapes.

The size of the flow channel that forms the flow channel structure of the present technology may be appropriately set by a person skilled in the art taking the size of the imaging targets into account, for example. The size of the imaging flow channel in the flow channel structure of the present technology may be set, with the field of view of the objective lens being taken into account.

In an embodiment of the flow channel structure according to the present technology, the shape of a cross-section of the imaging flow channel in the flow channel structure of the present technology may be the same as the shape of the field of view of the objective lens, or may be such a shape as to cover the entire field of view of the objective lens. For example, the area of a cross-section of the imaging flow channel may be larger than the area of the field of view of the objective lens, and may be 1.01 to 4 times, or particularly, 1.1 to 3 times, or more particularly, 1.2 to 2.5 times larger than the area of the field of view of the objective lens, for example.

Further, in another embodiment of the flow channel structure according to the present technology, the imaging flow channel in the flow channel structure of the present technology may have such a size that allows one to five imaging targets, or particularly, one to three imaging targets, or more particularly, one imaging target, such as a cell, to pass therethrough, for example.

In a case where a cross-section of the flow channel forming the flow channel structure of the present technology is circular, the diameter of the cross-section of the flow channel may be 0.1 to 10 mm, or particularly, 0.2 to 5 mm, or more particularly, 0.5 to 3 mm, for example. In a case where a cross-section of the flow channel forming the flow channel structure of the present technology is elliptical, the minor axis of the cross-section of the flow channel may be 0.1 to 10 mm, or particularly, 0.2 to 5 mm, or more particularly, 0.5 to 3 mm, for example.

In one embodiment of the flow channel structure of the present technology, in a case where the field of view of the objective lens is a circle, a cross-section of the imaging flow channel in the flow channel structure of the present technology may be a circle that has the same diameter as the diameter of the circle of the field of view of the objective lens, or may be a circle that has a larger diameter than the diameter of the circle of the field of view of the objective lens, such as a diameter 1.01 to 2 times, or particularly, 1.05 to 1.7 times, or more particularly, 1.1 to 1.5 times larger than the diameter of the circle of the field of view of the objective lens, for example. In a case where the field of view of the objective lens is a circle with a diameter of 1 mm, for example, a cross-section of the imaging flow channel in the flow channel structure of the present technology is a circle that has a diameter of 1 mm to 2 mm, or particularly, a diameter of 1.05 mm to 1.7 mm, or more particularly, a diameter of 1.1 to 1.5 mm, for example.

In a case where a cross-section of the flow channel forming the flow channel structure of the present technology is a square, a side of the cross-section of the flow channel may be 0.1 to 10 mm, or particularly, 0.2 to 5 mm, or more particularly, 0.5 to 3 mm, for example. In a case where a cross-section of the flow channel forming the flow channel structure of the present technology is rectangular, the short side of the cross-section of the flow channel may be 0.1 to 10 mm, or particularly, 0.2 to 5 mm, or more particularly, 0.5 to 3 mm, for example.

In one embodiment of the present technology, the flow channel structure of the present technology may include at least one fluid introduction channel that introduces a fluid into the imaging flow channel. That is, the fluid introduction channel continues to the imaging flow channel, and a fluid that has flowed in the fluid introduction channel flows into the imaging flow channel. The number of the fluid introduction channels is one to four, for example, but is preferably one or two, from the viewpoint of facilitation of manufacturing of the flow channel structure.

The direction of the fluid introduction channel may differ from the direction of the imaging flow channel. The direction of the fluid introduction channel is the direction of flow of the fluid flowing in the flow channel or the direction of the axis of the flow channel. In the present technology, in a case where a cross-section of the flow channel is circular or elliptical, the axis of the flow channel refers to the line passing through the center of the cross-section.

The direction of the fluid introduction channel may form an angle of 10 to 90 degrees, or preferably, 30 to 90 degrees, or more preferably, 45 to 90 degrees, or even more preferably, 60 to 90 degrees, with respect to the optical axis, for example. As the fluid introduction channel and the optical axis form such an angle, the fluid introduction channel does not block the space between the objective lens or the light source and the imaging flow channel, and thus, better observation can be performed.

In one embodiment of the present technology, the flow channel structure of the present technology includes at least two of the fluid introduction channels, or preferably two of the fluid introduction channels, and the at least two fluid introduction channels may merge on the optical axis. In this embodiment, the fluids flowing in the at least two fluid introduction channels merge and then flow into the imaging flow channel. The merged fluid flows in the optical axis direction in the imaging flow channel.

In one embodiment of the present technology, the flow channel structure of the present technology may include at least one fluid ejection channel that ejects the fluid having passed through the imaging flow channel to the outside of the flow channel structure. In other words, the fluid ejection channel continues from the imaging flow channel, and the fluid that has passed through the imaging flow channel is ejected out of the flow channel structure through the fluid ejection channel. The number of the fluid ejection channels is one to four, for example, but is preferably one or two, from the viewpoint of facilitation of manufacturing of the flow channel structure.

The direction of the fluid ejection channel may differ from the direction of the imaging flow channel. The direction of the fluid ejection channel is the direction of flow of the fluid flowing in the flow channel or the direction of the axis of the flow channel.

The direction of the fluid ejection channel may form an angle of 10 to 90 degrees, or preferably, 30 to 90 degrees, or more preferably, 45 to 90 degrees, or even more preferably, 60 to 90 degrees, with respect to the optical axis, for example. As the fluid ejection channel and the optical axis form such an angle, the fluid ejection channel does not block the space between the light source or the objective lens and the imaging flow channel, and thus, better observation can be performed.

In one embodiment of the present technology, the flow channel structure of the present technology includes at least two of the fluid ejection channels, or preferably two of the fluid ejection channels, and the at least two fluid ejection channels may branch from the imaging flow channel. In this embodiment, the fluid passing through the imaging flow channel flows into the at least two branched fluid ejection channels.

In one embodiment of the present technology, the flow channel structure may include a vibrator. The vibrator may be attached to an external wall surface of the fluid introduction channel or the imaging flow channel, for example. As the vibrator applies vibration to the flow channel structure, it is possible to prevent sedimentation of the imaging targets in the flow channel structure. In this embodiment, the region to which the focal point is adjusted in the imaging flow channel moves with vibration. Therefore, in this embodiment, the imaging timing and/or the phase of vibration is controlled so that the timing to perform imaging matches the phase of vibration. Thus, the influence of the vibration on the imaging is reduced.

The flow channel structure of the present technology may be formed with a material known in the art. Examples of the material that forms the flow channel structure of the present technology include, but are not limited to, polycarbonate, cycloolefin polymer, polypropylene, polydimethylsiloxane (PDMS), polymethylmethacrylate (PMMA), polyethylene, polystyrene, glass, and silicon.

The flow channel structure of the present technology may be manufactured by a method known in the art. For example, one substrate in which the fluid introduction channel and the imaging flow channel are formed and one substrate in which the imaging flow channel and the fluid ejection channel are formed are joined to each other so that the positions of the imaging flow channels coincide with each other. The flow channel structure of the present technology may be manufactured in this manner.

The present technology also provides an imaging member including the flow channel structure of the present technology. The imaging member may be a member to be used for imaging a sample through a microscope, for example. The imaging member may be a chip, a cartridge, or a slide glass, for example, but is not necessarily one of these members. The imaging member of the present technology may be manufactured by the manufacturing method described above regarding the flow channel structure, using the material described above regarding the flow channel structure.

(2) First Example (a Flow Channel Structure) of the First Embodiment

Figure 4:
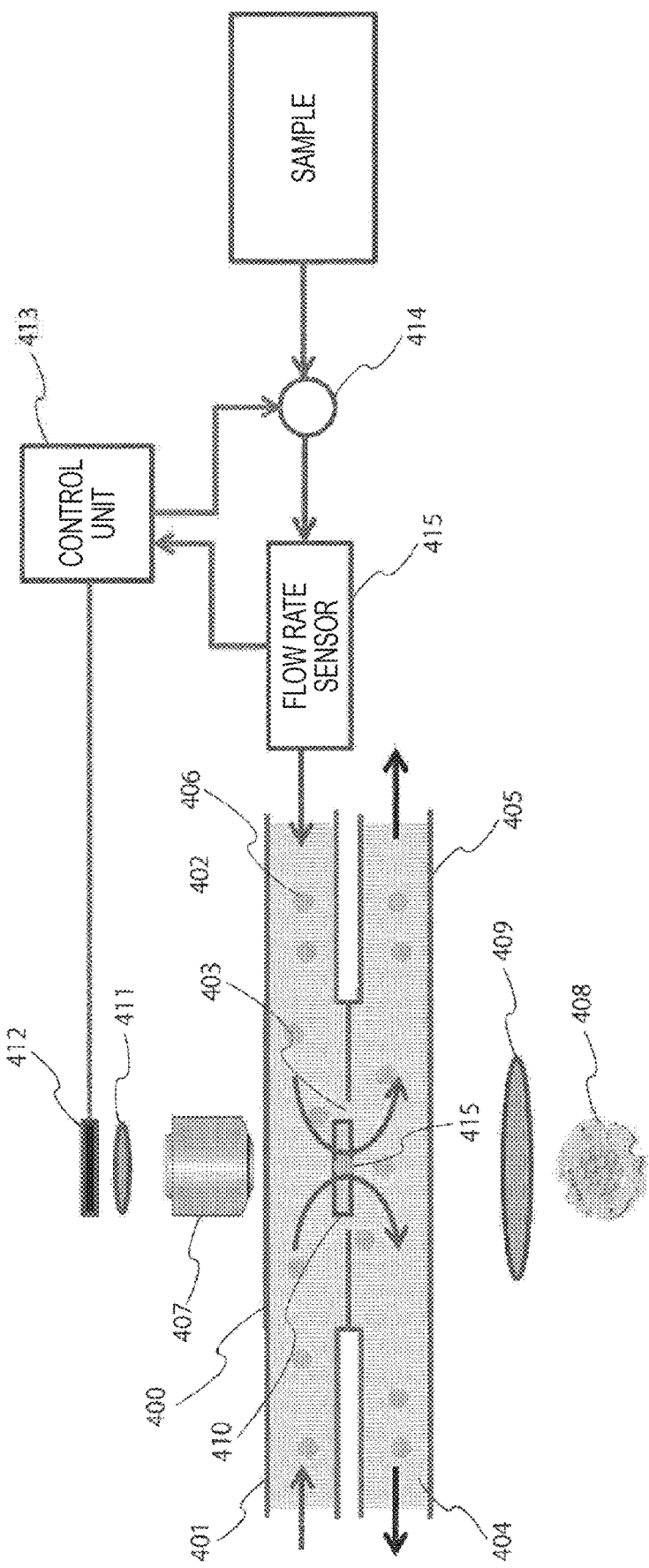
FIG. 4 is a schematic diagram showing a flow channel structure of the present technology and a state of imaging using the flow channel structure.

A flow channel structure of the present technology is described below with reference to FIG. 4. FIG. 4 is a schematic diagram showing a flow channel structure of the present technology and a state of imaging using the flow channel structure.

In FIG. 4, a flow channel structure 400 includes fluid introduction channels 401 and 402, an imaging flow channel 403, and fluid ejection channels 404 and 405. A fluid containing imaging targets 406 such as solid objects derived from a living organism flows in the flow channel structure 400, for example. An objective lens 407 and a light source 408 are disposed to sandwich the imaging flow channel 403. The directions of the fluid introduction channels 401 and 402 form an angle of 90 degrees with the optical axis of the objective lens 407. The directions of the fluid ejection channels 404 and 405 also form an angle of 90 degrees with the optical axis of the objective lens 407.

Light emitted from the light source 408 is applied to the imaging flow channel 403 through an illumination optical system 409. Further, in the imaging flow channel 403, there is a region 410 to which the focal point of the objective lens 407 is adjusted. An image of the region 410 can be observed through the objective lens 407. An image of the region 410 is acquired as image data by an image sensor 412 through an imaging optical system 411. The acquired image data is sent from the image sensor 412 to a control unit 413.

Introduction of a fluid into the liquid introduction channels 401 and 402 is conducted by a pump 414. The flow velocity of the fluid is measured by a flow rate sensor 415. Data regarding the flow velocity of the fluid measured by the flow rate sensor 415 is sent to the control unit 413. On the basis of the data regarding the flow velocity, the control unit 413 controls the amount of liquid to be sent by the pump 414 or the like, for example. As a result, the flow velocity of the fluid is controlled.

In the present technology, any clear boundary is not necessarily set between the fluid introduction channels and the imaging flow channel. For example, if a flow channel includes a region in which imaging according to the present technology is to be performed, the flow channel can be regarded as an imaging flow channel. If the flow channel causes a fluid to flow into the region, the flow channel can be regarded as a fluid introduction channel. Further, in the present technology, any clear boundary is not necessarily set between the imaging flow channel and the fluid ejection channels. For example, if a flow channel includes a region in which imaging according to the present technology is to be performed, the flow channel can be regarded as an imaging flow channel. If the flow channel ejects a fluid that has passed through the imaging flow channel to the outside of the flow channel structure, the flow channel can be regarded as a fluid ejection channel.

The fluid in the fluid introduction channels 401 and 402 flows toward the optical axis of the objective lens 407. The flows in the fluid introduction channels 401 and 402 then merge on the optical axis, and further flow into the imaging flow channel 403. The fluid that has passed through the imaging flow channel 403 branches and flows into the fluid ejection channels 404 and 405. In the imaging flow channel 403, there is the region 410 to which the focal point of the objective lens 407 is adjusted. In the region 410, the fluid flows in the same direction as the optical axis. In a case where an image of the region 410 is captured through the objective lens 407, an image of an imaging target passing through the region 410 at the time of this imaging is obtained. In a case where imaging is performed in the state shown in FIG. 4, an image of an imaging target 415 is obtained.

In FIG. 4, imaging of the region 410 through the objective lens 407 is performed a plurality of times successively while a fluid is made to flow. As image data is processed so that the images obtained through the successive imaging are superimposed on one another, stereoscopic image data shown in FIG. 3 is created.

For example, in a case where the numerical aperture NA of the objective lens is 0.5, the depth of field is approximately 4 μm. Therefore, image data is processed so that images obtained by performing imaging every time the imaging targets move approximately 4 μm are superimposed on one another. As a result, stereoscopic image data of the imaging targets is obtained. In a case where the depth of field is 4 μm, and the flow velocity in the region 410 is 0.5 mm/s, the imaging frame rate is set to 0.5 mm/s÷4 μm=125 fps (the number of frames per second), so that a plurality of sets of image data suitable for producing stereoscopic image data is obtained. Further, in a case where the depth of field and the imaging frame rate are fixed, the flow velocity is set to a predetermined value, so that a plurality of sets of image data suitable for creating stereoscopic image data can be obtained.

Note that the flow velocity in the imaging flow channel 402 may be the highest at the central portion of the flow channel, and may be lower at a portion closer to a wall surface of the flow channel. The imaging frame rate may be set on the basis of the highest flow velocity at the central portion of the flow channel, for example. With this, it becomes possible to create stereoscopic image data at portions with lower flow velocities.

(3) Second Example (a Flow Channel Structure) of the First Embodiment

Figure 5:
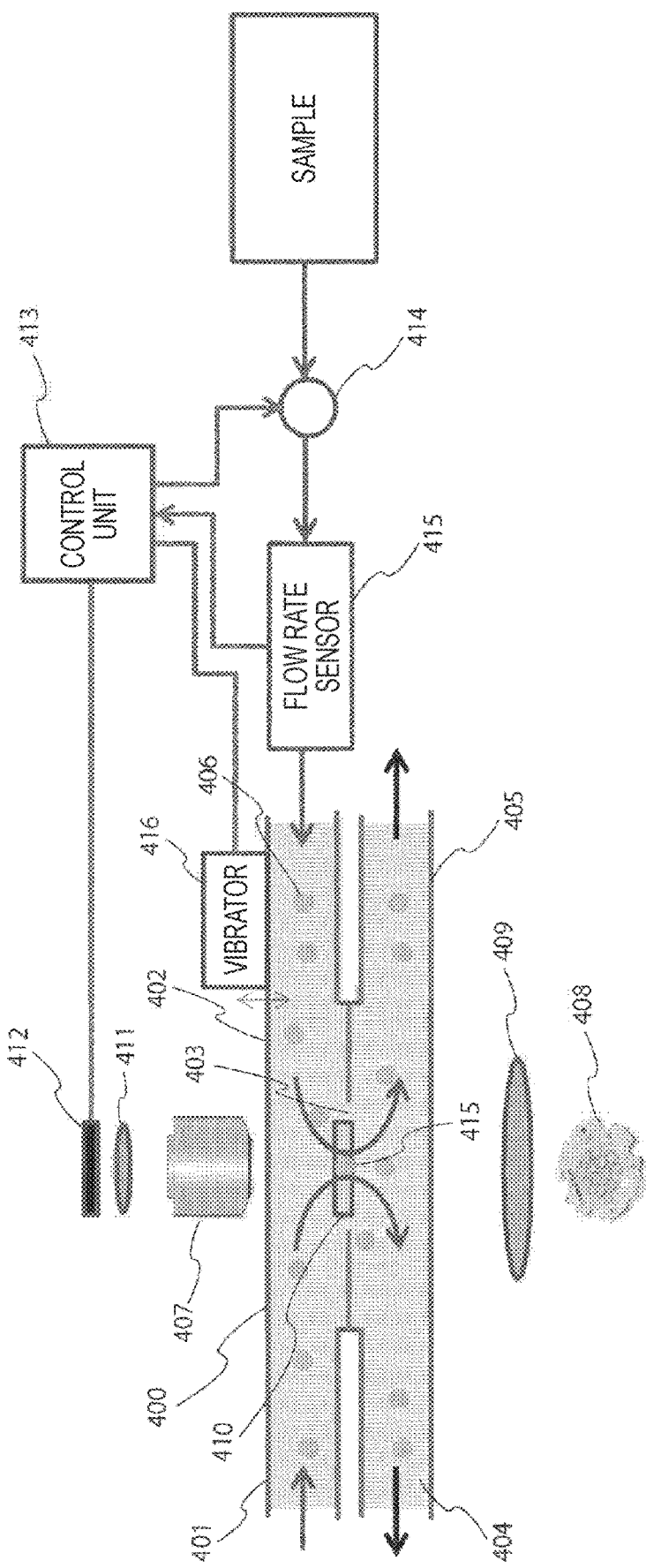
FIG. 5 is a schematic diagram showing a flow channel structure of the present technology and a state of imaging using the flow channel structure.

Another example of a flow channel structure of the present technology is now described with reference to FIG. 5. FIG. 5 is a schematic diagram showing a flow channel structure of the present technology and a state of imaging using the flow channel structure.

FIG. 5 is the same as FIG. 4, except that the flow channel structure 400 includes a vibrator 416 connected to the control unit 413. In FIG. 5, the vibrator 416 vibrates the flow channel structure. The vibrator is a piezo-vibrator, for example. The vibration of the vibrator 416 prevents sedimentation of the imaging targets in the flow channel, particularly in a case where imaging targets having a high specific gravity are made to flow in the flow channel.

Further, the vibrator 415 is connected to the control unit 413. The control unit 413 synchronizes the phase of vibration with the timing of imaging. With this, a region to which the focal point is adjusted can be fixed for the objective lens. As a result, the influence of vibration on imaging is reduced.

(4) Third Example (a Flow Channel Structure) of the First Embodiment

Figure 6:
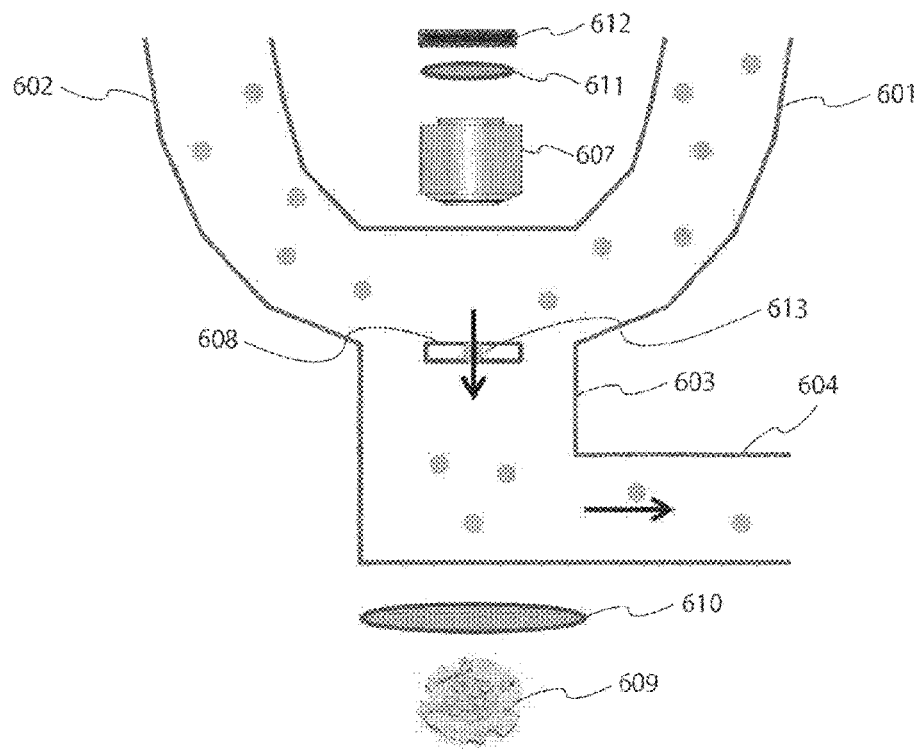
FIG. 6 is a schematic diagram showing a flow channel structure of the present technology and a state of imaging using the flow channel structure.

Another example of a flow channel structure of the present technology is now described with reference to FIG. 6. FIG. 6 is a schematic diagram showing a flow channel structure of the present technology and a state of imaging using the flow channel structure.

In FIG. 6, a flow channel structure 600 includes fluid introduction channels 601 and 602, an imaging flow channel 603, and a fluid ejection channel 604. Imaging targets 606, such as solid objects derived from a living organism, flow in the flow channel structure 600, for example. An objective lens 607 and a light source 609 are disposed to sandwich the imaging flow channel 603. The directions of the fluid introduction channels 601 and 602 may form an angle smaller than 90 degrees with the optical axis of the objective lens 607. In FIG. 6, the directions form an angle of about 30 to 90 degrees. Meanwhile, the direction of the fluid ejection channel 604 may form an angle of 45 to 90 degrees with respect to the optical axis, for example. In FIG. 6, the direction forms an angle of 90 degrees. Although one fluid ejection channel is shown in FIG. 6, another fluid ejection channel may be provided on the opposite side from the fluid ejection channel 604, for example. The light source 609, an illumination optical system 610, and an imaging optical system 611 may be appropriately disposed to enable imaging of a region 608 through the objective lens 607.

Light emitted from the light source 609 is applied to the imaging flow channel 603 through the illumination optical system 610. Further, in the imaging flow channel 603, there is the region 608 to which the focal point of the objective lens 607 is adjusted. An image of the region 608 can be observed through the objective lens 607. An image of the region 608 is acquired as image data by an image sensor 612 through the imaging optical system 611. The acquired image data is sent from the image sensor 612 to a control unit (not shown).

The fluid in the fluid introduction channels 601 and 602 flows toward the imaging flow channel 603, or flows closer to the optical axis. The flows in the fluid introduction channels 601 and 602 then merge on the optical axis, and further flow into the imaging flow channel 603. The fluid that has passed through the imaging flow channel 603 flows into the fluid ejection channel 604. In the imaging flow channel 603, there is the region 608 to which the focal point of the objective lens 607 is adjusted. In the region 608, the fluid flows in the same direction as the optical axis. In a case where an image of the region 608 is captured through the objective lens 607, an image of an imaging target present in the region 608 at the time of this imaging is obtained. In a case where imaging is performed in the state shown in FIG. 6, an image of an imaging target 613 is obtained.

In FIG. 6, imaging of the region 608 through the objective lens 607 is performed a plurality of times successively while a fluid is made to flow. As image data is processed so that the images obtained through the successive imaging are superimposed on one another, stereoscopic image data shown in FIG. 3 is created.

Further, in the flow channel structure in FIG. 6, the direction of flow in the imaging flow channel may be set in the same manner as the direction of action of gravity. This can prevent particles from settling and depositing in the flow channel. As a result, clogging of the flow channel is avoided.

In the flow channel structure in FIG. 6, the flow velocity of the fluid may be controlled by a pump. Alternatively, in a case where the flow channel structure is disposed so that the direction of the optical axis becomes the same as the direction of action of gravity, it is possible to control the flow velocity of the fluid by controlling the difference between the height of the inlet into which the fluid is to be introduced and the height of the outlet from which the fluid is to be ejected.

(5) Fourth Example (a Flow Channel Structure) of the First Embodiment

Figure 7:
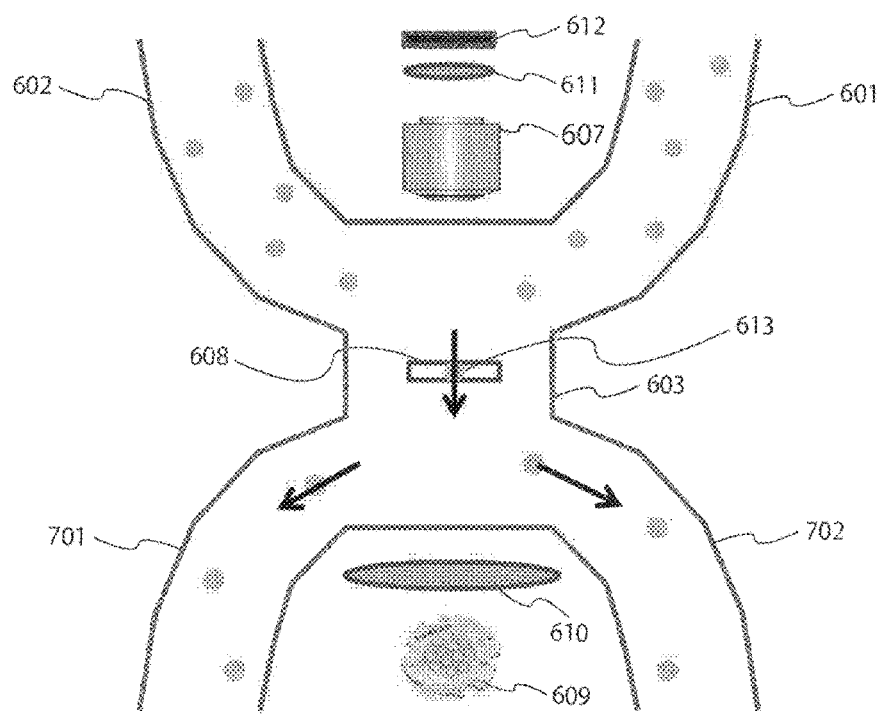
FIG. 7 is a schematic diagram showing a flow channel structure of the present technology and a state of imaging using the flow channel structure.

Another example of a flow channel structure of the present technology is now described with reference to FIG. 7. FIG. 7 is a schematic diagram showing a flow channel structure of the present technology and a state of imaging using the flow channel structure.

This embodiment is the same as that shown in FIG. 6, except that two fluid ejection channels 701 and 702 are provided in place of the single fluid ejection channel 604. As the fluid ejection channel is made to branch in this manner, the flow of a fluid that has passed through the imaging flow channel can be made smoother.

(6) Fifth Example (a Flow Channel Chip) of the First Embodiment

Figure 8:
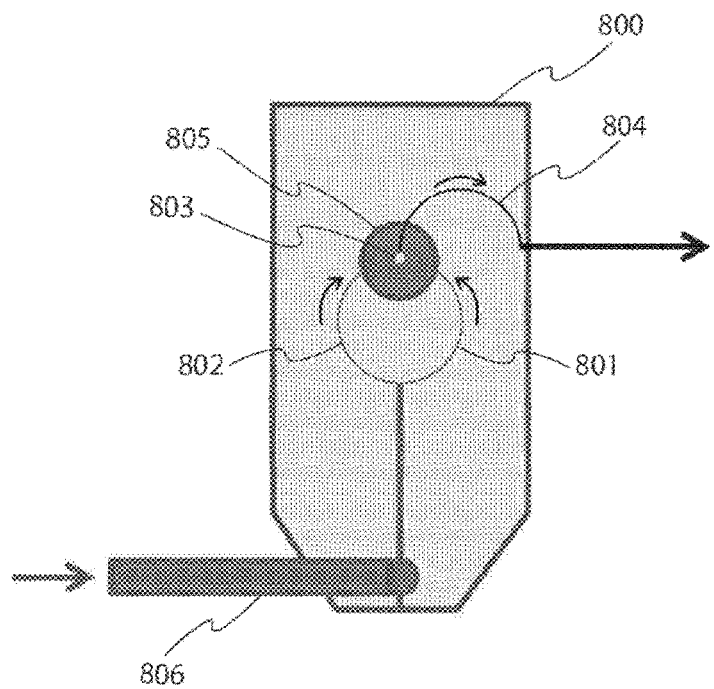
FIG. 8 is a schematic view of an imaging member of the present technology.

An example of an imaging member of the present technology is now described with reference to FIG. 8. FIG. 8 is a schematic view of an imaging member of the present technology.

In FIG. 8, an imaging flow channel chip 800 includes fluid introduction channels 801 and 802, an imaging flow channel 803, and a fluid ejection channel 804. Imaging in the imaging flow channel chip 800 is performed in a state in which an objective lens is disposed on the near or far side of the paper surface, and a light source is disposed on the far or near side of the paper surface. A fluid flows in the optical axis direction in the imaging flow channel 803. In other words, the fluid flows from the near side to the far side of the paper surface, or from the far side to the near side. A region 805 can be observed through the objective lens of a microscope. The directions of the fluid introduction channels 801 and 802 form an angle of 90 degrees with the optical axis of the objective lens. The direction of the fluid ejection channel 804 also forms an angle of 90 degrees with the optical axis of the objective lens. The directions of the fluid introduction channels 801 and 802 form an angle of 90 degrees with the direction of the fluid ejection channel 804. A fluid is supplied into the flow channel chip 800 through a tube 806 by a pump (not shown) connected to the tube 806, for example. The focal point of the objective lens is adjusted to a region in the imaging flow channel 803. Imaging targets flow in the same direction as the optical axis in the imaging flow channel 803, and an image of an imaging target present in the region at the time of imaging is obtained.

(7) Sixth Example (a Flow Channel Chip) of the First Embodiment

Figure 9:
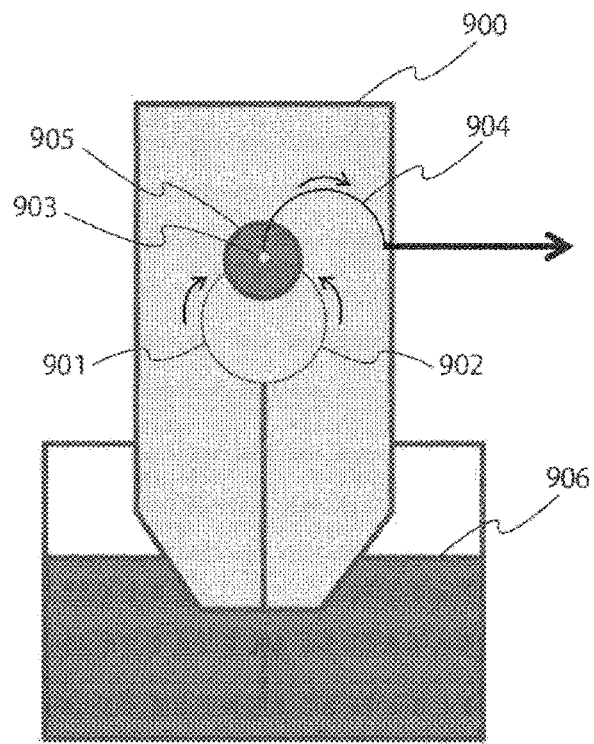
FIG. 9 is a schematic view of an imaging member of the present technology.

An example of an imaging member of the present technology is now described with reference to FIG. 9. FIG. 9 is a schematic view of an imaging member of the present technology.

In FIG. 9, an imaging flow channel chip 900 includes fluid introduction channels 901 and 902, an imaging flow channel 903, and a fluid ejection channel 904. Imaging in the imaging flow channel chip 900 is performed in a state in which an objective lens is disposed on the near or far side of the paper surface, and a light source is disposed on the far or near side of the paper surface. A fluid flows in the optical axis direction in the imaging flow channel 903. In other words, the fluid flows from the near side to the far side of the paper surface, or from the far side to the near side. A region 905 can be observed through the objective lens of a microscope. The directions of the fluid introduction channels 901 and 902 form an angle of 90 degrees with the optical axis of the objective lens. The direction of the fluid ejection channel 904 also forms an angle of 90 degrees with the optical axis of the objective lens. The directions of the fluid introduction channels 901 and 902 form an angle of 90 degrees with the direction of the fluid ejection channel 904. The flow channel chip 900 is in direct contact with a fluid 906 containing the imaging targets. A pump (not shown) is connected to the downstream side of the fluid ejection channel 904. The fluid is introduced into the flow channel chip 900 by a suction force of the pump.

The flow channel chip 900 in FIG. 9 is in direct contact with the fluid. A flow channel chip is replaced for each fluid, so that contamination between fluids is avoided.

4. Second Embodiment (Imaging Method)

(1) Description of the Second Embodiment

The present technology provides an imaging method that includes imaging an imaging target in an imaging flow channel in which a fluid containing the imaging target flows in the same direction as the optical axis of an objective lens. In other words, when an image of a region in the imaging flow channel is captured through an objective lens while the focal point of the objective lens is adjusted to the region, an image of an imaging target present in the region is captured. In the imaging method of the present technology, a fluid containing imaging targets flows in the same direction as the optical axis of the objective lens in the imaging flow channel. After the focal point is adjusted to the predetermined region, it is not necessary to carry out the step of adjusting the focal point to an imaging target by operating the objective lens.

The imaging flow channel to be used in the imaging method of the present technology is as described above in "3. First embodiment (a flow channel structure and an imaging member)", and therefore, explanation of the imaging flow channel structure is not made herein.

In one embodiment of the imaging method of the present technology, the imaging may be performed in a state in which the position of the imaging flow channel is fixed with respect to the objective lens. More specifically, the imaging may be performed in a state in which the region in the imaging flow channel is fixed with respect to the objective lens. In other words, in the imaging method of the present technology, after the focal point is adjusted to the region, it is not necessary to adjust the focal point to an imaging target by operating the objective lens.

In the present technology, a state in which the position of the imaging flow channel is fixed with respect to the objective lens means that the relative positional relationship between the position and the objective lens at the time of imaging is fixed. In the fixed state, the position of the imaging flow channel may be physically fixed with respect to the objective lens, and the position of the imaging flow channel may be the same with respect to the objective lens between respective imaging operations. The latter example is a case where the imaging flow channel is vibrated at predetermined intervals by a vibrator, and the phase of the vibration by the vibrator is synchronized with the intervals of imaging through the objective lens, for example. As the phase is synchronized with the imaging intervals, the region to which the focal point is adjusted in imaging through the objective lens can be the same between respective imaging operations.

In one embodiment of the imaging method of the present technology, the imaging may be performed a plurality of times. In the imaging method of the present technology, a fluid containing imaging targets flows in the same direction as the optical axis of the objective lens in the imaging flow channel. Accordingly, as imaging is performed a plurality of times, it is possible to obtain image data containing at least the same amount of information as that in a case where images of a plurality of fields of view, or more particularly, digital images, are obtained, without mechanically moving the stage of the microscope in the X direction and/or the Y direction as described above in "1. Description of a conventional technology".

Furthermore, the imaging may be performed successively the plurality of times. As image data is processed so that the images obtained through the imaging performed successively the plurality of times are superimposed on one another, stereoscopic image data shown in FIG. 3 is obtained. It becomes possible to more accurately grasp the three-dimensional shape of each imaging target, on the basis of the stereoscopic image data.

A technique known to those skilled in the art may be used as the technique for processing image data so that images obtained by imaging performed successively a plurality of times are superimposed on one another. An example of the technique may be a technique relating to so-called Z-stacks. The technique may be a technique disclosed in Japanese Patent Application Laid-Open No. 2017-058704, for example, but is not limited to that disclosed in this literature.

In one embodiment of the imaging method of the present technology, the next imaging may be performed after the imaging targets move a distance equivalent to the depth of field in the optical axis direction after imaging. In other words, in one embodiment of the imaging method of the present technology, an imaging interval may be the time required for an imaging target to move a distance equivalent to the depth of field in the optical axis direction.

Specifically, in one embodiment of the imaging method of the present technology, the frame rate in the imaging performed the plurality of times is equal to or higher than the numerical value of the quotient obtained by dividing the flow velocity of the fluid in the region to which the focal point is adjusted in the imaging by the depth of field.

When the imaging frame rate, the flow velocity, and the depth of field satisfy this relationship, it becomes possible to create more accurate stereoscopic image data by superimposing a plurality of sets of obtained image data. The relationship is preferably satisfied in at least part of the region. The relationship is preferably satisfied in the portion with the highest flow velocity in the region, such as the central portion of a cross-section of the imaging flow channel, for example.

In another embodiment of the imaging method of the present technology, an imaging interval may be longer or shorter than the time required for an imaging target to move a distance equivalent to the depth of field in the optical axis direction. The imaging interval may be selected as appropriate by a person skilled in the art, in accordance with desired image data.

The imaging method of the present technology may further include obtaining an image relating to the three-dimensional shape of the imaging target, on the basis of image data obtained through the imaging performed the plurality of times. With this, it becomes possible to more accurately grasp the three-dimensional shape of each imaging target. With stereoscopic images of imaging targets obtained by the imaging method of the present technology, it becomes possible to more accurately analyze cells, for example. In addition to that, with more accurately obtained stereoscopic images of cells, it also becomes possible to automatically analyze cells.

In one embodiment of the imaging method of the present technology, the imaging method of the present technology may further include analyzing image data obtained by the imaging. For example, in the analysis, data regarding the size, the color, and/or the planar or three-dimensional shape of imaging targets is obtained on the basis of the image data of the imaging targets. Further, the type of the imaging targets may be determined on the basis of the data. Furthermore, in the analysis, the number of the imaging targets, or more particularly, the number of the imaging targets of a specific type may be counted on the basis of the image data of the imaging targets. The rate of content of specific imaging targets in a fluid having a predetermined volume may be calculated on the basis of the count result. Furthermore, a distribution condition regarding the size of the imaging targets, such as a particle size distribution, may be determined on the basis of the count result, for example.

Further, in the analysis, on the basis of the determined type and the determined number of the imaging targets, it is possible to determine whether an individual such as a human who provided the fluid containing the imaging targets has a disease, for example, and determine the type of the disease detected in the individual and the physical condition of the individual.

For example, in a case where the fluid is urine or a urine-derived sample, the imaging targets are of one or two types of the following solid components: red blood cells, white blood cells, platelets, other cells such as epithelial cells, columnar cells, and cancer cells, and crystals such as uric acid crystals. In the above analysis, it is possible to determine of which type of the solid components the imaging targets are, on the basis of the obtained image data. Further, in the above analysis, the number of the solid components in a predetermined amount of urine is counted on the basis of the obtained image data.

Furthermore, based on the type and the number of solid components contained in the urine or the urine-derived sample, it is possible to determine whether the individual such as a human who provided the urine or the urine-derived sample has a disease, for example, and determine the type of the disease detected in the individual and the physical condition of the individual.

Examples of diseases to be determined include, but are not limited to, nephritis, nephritic calculi, kidney tumors, cardiac failure, arteriosclerosis, urinary tract inflammation, urinary tract calculi, urinary tract tumors, nephrotic syndrome, urethritis, cystitis, and hypertension.

In conventional urinary sediment, physical conditions are determined, or a specific disease is detected, on the basis of the number of specific cells in a predetermined number of fields of view. In the present technology, it is possible to more accurately count solid components. Thus, physical conditions can be more accurately determined, or a specific disease can be more accurately detected.

(2) First Example (an Imaging Method) of the Second Embodiment

Figure 10:
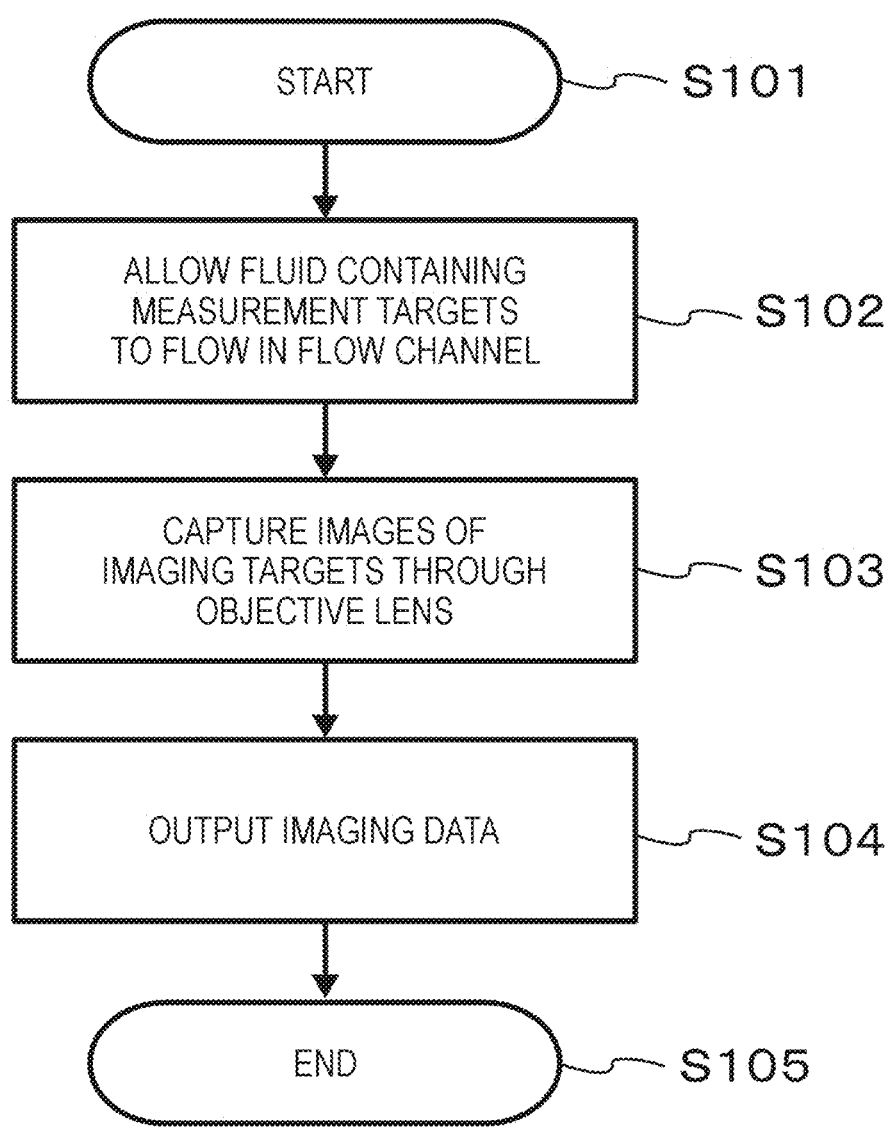
FIG. 10 is a flowchart of an imaging method of the present technology.

An imaging method of the present technology is described below, with reference to FIG. 10. FIG. 10 is a flowchart of the imaging method of the present technology.

In step S101, the imaging method of the present technology is started.

In step S102, a fluid containing imaging targets is made to flow in an imaging flow channel. For example, the fluid may flow from a fluid introduction channel located on the upstream side of the imaging channel into the imaging flow channel, and then flow into a fluid ejection channel located on the downstream side of the imaging flow channel. The flow velocity of the fluid may be controlled by a pump, for example. The pump may be selected as appropriate by a person skilled in the art. The pump may be connected to the upstream side of the fluid introduction channel or the downstream side of the fluid ejection channel, for example.

In step S103, imaging of an imaging target via an objective lens is performed. The objective lens may be provided in a microscope, for example. The microscope may be an optical microscope, for example, but is not necessarily an optical microscope. The type of the objective lens may be selected as appropriate by a person skilled in the art, depending on the imaging targets. Imaging may be performed by an imaging device equipped with an image sensor, such as a digital camera, for example. The image sensor may be a charge coupled device (CCD) or a complementary metal oxide semiconductor (CMOS), for example. An image obtained by imaging may be stored into the imaging device, or may be stored into an external data storage device connected to the imaging device in a wired or wireless manner.

In step S103, a plurality of sets of image data obtained by imaging performed a plurality of times may be processed so as to form stereoscopic images of the imaging targets. The data regarding the three-dimensional shape of the imaging targets obtained by the above processing may be then stored into the above mentioned imaging device or the above mentioned data storage device.

Step S103 may be carried out at the same time as step S102.

In step S104, the images of the imaging targets obtained in S103 are output. Step S104 is carried out as needed, and the imaging method of the present technology may be ended, with step S104 not carried out. The output may be performed by an image output unit such as a display connected to the imaging device in a wired or wireless manner, or by an external output device such as a printing device connected to the imaging device in a wired or wireless manner, for example. On the basis of the output images, the cells subjected to the imaging may be analyzed by a healthcare professional, for example.

In step S105, the imaging method is ended.

(3) Second Example (an Imaging Method) of the Second Embodiment

Figure 11:
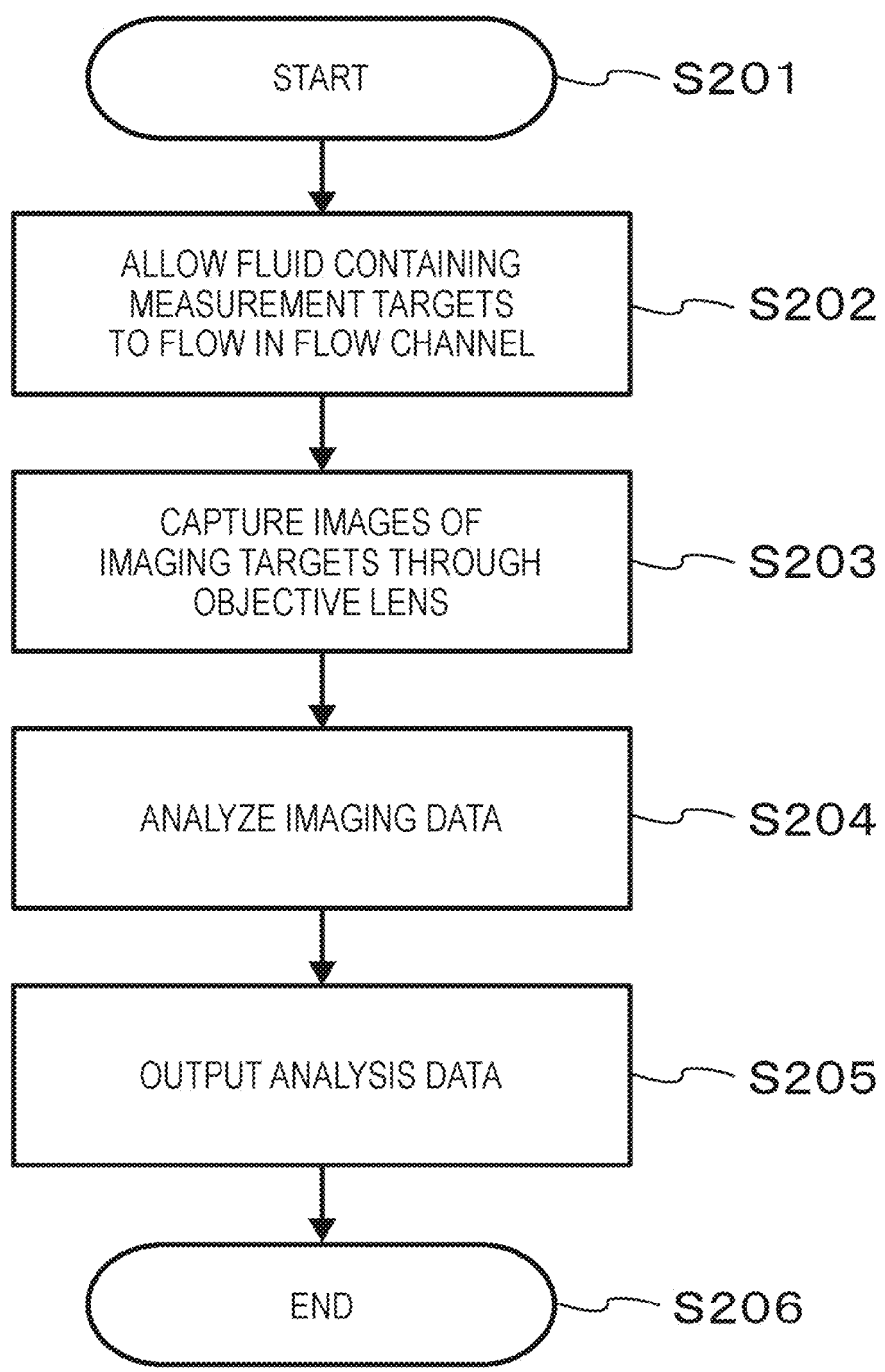
FIG. 11 is a flowchart of an imaging method of the present technology.

An imaging method of the present technology is described below, with reference to FIG. 11. FIG. 11 is a flowchart of the imaging method of the present technology. S201 through S203 in FIG. 11 are the same as S101 through S103 in FIG. 10, and S206 is the same as S105 in FIG. 10. Therefore, explanation of S201 through S203 and S206 is not made herein.

In step S204, captured data is analyzed. The imaging data may be analyzed by an analysis unit or the like provided in the above mentioned imaging device, or may be analyzed by an external analysis device or the like connected to the imaging device in a wired or wireless manner. Specific examples of content of the analysis are as described above in "(1) Description of the second embodiment".

Further, in step S204, the stereoscopic image formation process described above in regard to step S103 in "(1) Description of the second embodiment" may be performed.

In step S205, the result of the analysis in step S204 is output. In step S205, in addition to the analysis result, image data obtained by imaging may also be output.

5. Third Embodiment (an Imaging Target Analysis Device)

(1) Description of the Third Embodiment

The present technology provides an imaging target analysis device that includes: an imaging member including a flow channel structure including an imaging flow channel in which a fluid containing imaging targets flows in the same direction as the optical axis of an objective lens; and an imaging unit that performs imaging of the imaging targets through the objective lens.

The imaging member included in the imaging target analysis device of the present technology is as described above in "3. First embodiment (a flow channel structure and an imaging member)", and therefore, explanation of the imaging member is not made herein.

The imaging target analysis device of the present technology includes an imaging unit that performs imaging of imaging targets via an objective lens. Examples of such imaging target analysis devices include, but are not limited to, microscopes, and more particularly, optical microscopes. The imaging unit may include an objective lens, an imaging optical system, and an image sensor, for example. Image data regarding an image of an imaging target is acquired by the image sensor through the objective lens and the imaging optical system.

In one embodiment of the present technology, the imaging member may be replaceable. As the imaging member is replaceable, contamination of samples subjected to imaging can be avoided, for example. In view of this, the replaceable imaging member is particularly beneficial in analysis of human biological samples and evaluation of human health conditions.

(2) Example of the Third Embodiment (an Imaging Target Analysis Device)

Figure 12:
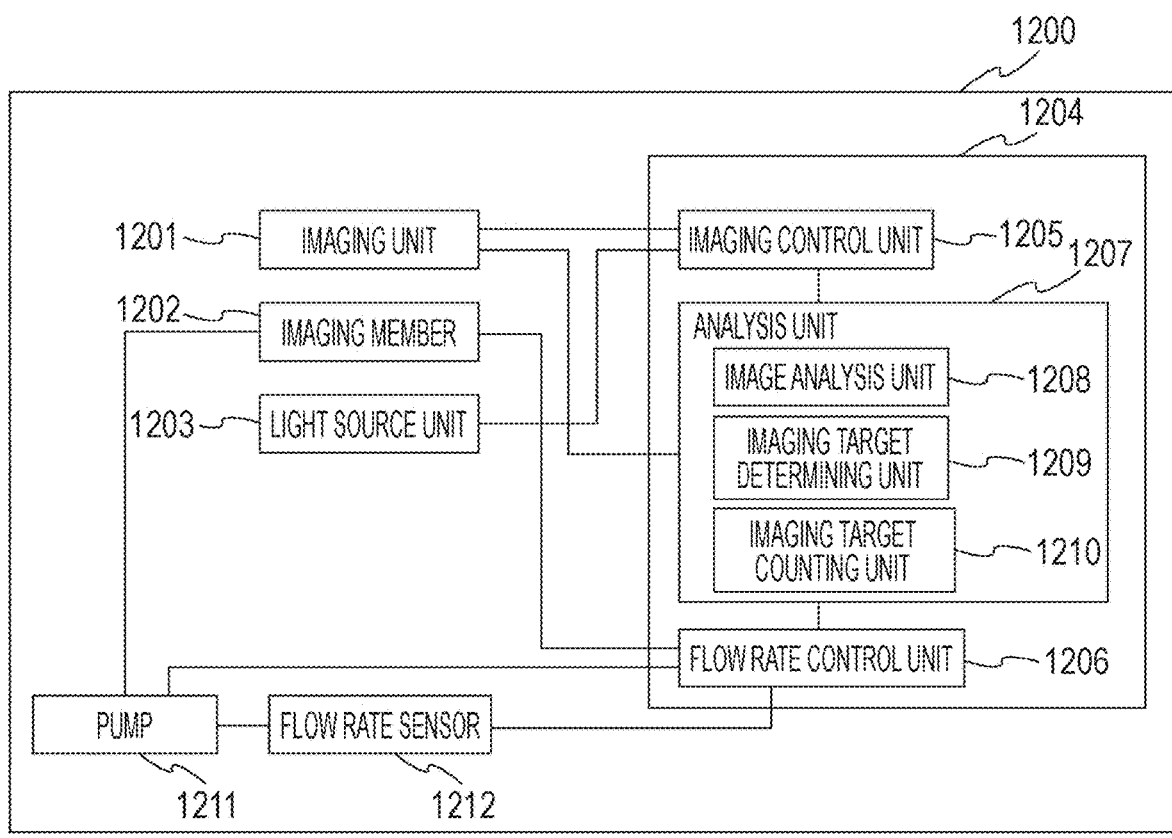
FIG. 12 is a block diagram of an imaging target analysis device of the present technology.

An example of an imaging target analysis device of the present technology is now described with reference to FIG. 12. FIG. 12 is a block diagram of an imaging target analysis device of the present technology.

As shown in FIG. 12, an imaging target analysis device 1200 of the present technology includes an imaging unit 1201 and an imaging member 1202. The imaging target analysis device 1200 may further include a light source unit 1203 and a control unit 1204. The control unit 1204 may include an imaging control unit 1205, a flow rate control unit 1206, and an analysis unit 1207. The analysis unit 1207 may include an image analysis unit 1208, an imaging target determining unit 1209, and an imaging target counting unit 1210. Furthermore, the imaging target analysis device 1200 may further include a pump 1211 and a flow rate sensor 1212. These components may be included in one device, or may be included in a plurality of devices and be connected so as to achieve the effects of the present technology.

The imaging unit 1201 includes an objective lens. The imaging unit 1201 may include an imaging device for performing imaging of imaging targets in an imaging flow channel in the imaging member 1202. The imaging unit 1201 carries out steps S103 and S203 described above in "4. Second embodiment (an imaging method)", for example. The imaging unit 1201 may include a data storage device (not shown).

The imaging member 1202 includes the imaging flow channel in which a fluid containing imaging targets flows. The focal point of the objective lens included in the imaging unit 1201 may be adjusted to a portion in the imaging flow channel. The imaging member 1202 is as described above in "3. First embodiment (a flow channel structure and an imaging member)", for example.

The light source unit 1203 emits light to the fluid, or more particularly, the imaging targets, flowing in the imaging flow channel in the imaging member 1202, for example, to enable the imaging unit 1201 to perform imaging of the imaging targets. The light source unit 1203 applies light to the imaging targets in the imaging in steps S103 and S203 described above in "4. Second embodiment (an imaging method)". The light source unit may include a light source and an illumination optical system, for example. The light source may be an LED, for example, but is not necessarily an LED. The illumination optical system may be one used in a conventional microscope.

The control unit 1204 may include the imaging control unit 1205, the flow rate control unit 1206, and the analysis unit 1207. Further, the control unit 1204 may be connected to an output unit (not shown) in a wired or wireless manner. The output unit may output image data acquired by the imaging unit 1201 and/or a result of analysis carried out by the analysis unit 1207. The output unit may be included in the imaging target analysis device 1200.

The imaging control unit 1205 controls imaging to be performed by the imaging unit 1202. For example, the imaging control unit 1205 may control imaging to be performed by the imaging unit 1202 in steps S103 and S203 described above in "4. Second embodiment (an imaging method)". The imaging control unit 1205 may control the imaging unit 1201 so that imaging is performed successively a plurality of times at predetermined time intervals, for example. Further, the imaging control unit 1205 may control the imaging unit 1201 so that the imaging unit 1201 performs imaging in synchronization with the phase of vibration caused by a vibrator (not shown) included in the imaging member 1202, for example.

The flow rate control unit 1206 controls the flow velocity and/or the flow rate of the fluid flowing in a flow channel, such as an imaging flow channel, in the imaging member 1202, for example. The flow rate control unit 1206 may control the supply of the fluid into the imaging flow channel by the pump 1210 in steps S102 and S202 described above in "4. Second embodiment (an imaging method)", for example. The flow rate control unit 1206 may control the amount of liquid to be supplied by the pump 1211, on the basis of the flow rate measured by the flow rate sensor 1212, for example.

The analysis unit 1207 may include the image analysis unit 1208, the imaging target determining unit 1209, and/or the imaging target counting unit 1210. The analysis unit 1207 may analyze the imaging data in step S204 described above in "4. Second embodiment (an imaging method)", and the analysis unit 1207 may also perform processing for forming stereoscopic images of imaging targets in step S103 described above in "4. Second embodiment (an imaging method)", for example.

The image analysis unit 1208 analyzes image data obtained by the imaging unit 1201. Further, the image analysis unit 1208 may also perform the processing for forming stereoscopic images of imaging targets described above in regard to step S103 in "4. Second embodiment (an imaging method)". The image analysis unit 1208 may acquire data regarding the shape, or particularly, the three-dimensional shape, the color, and the size of the imaging targets. The acquired data may be stored into a data storage device that is located outside the imaging target analysis device 1200 and is connected to the analysis unit in a wired or wireless manner, or into a data storage device (not shown) included in the imaging target analysis device 1200.

The imaging target determining unit 1209 may determine the type of the imaging targets, on the basis of the data regarding the imaging targets acquired by the image analysis unit 1208. For example, the imaging target determining unit 1209 may determine which cells the imaging targets are, whether the imaging targets is solid objects other than cells, and/or what crystals the imaging targets are. Data regarding the result of the determination may be stored into a data storage device that is located outside the imaging target analysis device 1200 and is connected to the analysis unit in a wired or wireless manner, or into a data storage device (not shown) included in the imaging target analysis device 1200.

The imaging target counting unit 1210 counts the number of specific cells or specific solid objects determined by the imaging target determining unit 1209. For example, in a case where the fluid to be subjected to imaging is urine or a urine-derived sample, the imaging target counting unit 1210 counts the number of cells of at least one of the following types: red blood cells, white blood cells, platelets, crystals, other cells such as epithelial cells, columnar cells, and cancer cells, and bacteria. Data regarding the result of the counting may be stored into a data storage device that is located outside the imaging target analysis device 1200 and is connected to the analysis unit in a wired or wireless manner, or into a data storage device (not shown) included in the imaging target analysis device 1200.

6. Fourth Embodiment (an Imaging Target Analysis System)

(1) Description of the Fourth Embodiment

The present technology provides an imaging target analysis system that includes: an imaging member including a flow channel structure including an imaging flow channel in which a fluid containing imaging targets flows in the same direction as the optical axis of an objective lens; and an imaging unit that performs imaging of the imaging targets through the objective lens.

The imaging member included in the imaging target analysis system of the present technology is as described above in "3. First embodiment (a flow channel structure and an imaging member)", and therefore, explanation of the imaging member is not made herein.

Further, the imaging unit included in the imaging target analysis system of the present technology is as described above in "5. Third embodiment (an imaging target analysis device)", and therefore, explanation of the imaging unit is not made herein.

(2) Example of the Fourth Embodiment (an Imaging Target Analysis System)

The imaging target analysis system of the present technology includes the imaging unit 1201 and the imaging member 1202 described above in "5. Third embodiment (an imaging target analysis device)" with reference to FIG. 12. The imaging unit 1201 and the imaging member 1201 may not be provided in one device. For example, the imaging target analysis system of the present technology may be a system in which a device including the imaging unit 1201 and a device (a microscope, for example) including the imaging member 1201 are designed to be able to implement an imaging method of the present technology.

The imaging target analysis system of the present technology may also include the light source unit 1203, the control unit 1204, the pump 1211, and the flow rate sensor 1212 described above in "5. Third embodiment (an imaging target analysis device)" with reference to FIG. 12. These components may not be provided in one device. The imaging target analysis system of the present technology may be a system in which these components are designed to be able to implement an imaging method of the present technology.

Note that the present technology may also be embodied in the configurations described below.

[1] An imaging target analysis device including:
an imaging member that includes a flow channel structure including an imaging flow channel in which a fluid containing an imaging target flows in the same direction as an optical axis of an objective lens; and
an imaging unit that performs imaging of the imaging target through the objective lens.

[2] The imaging target analysis device according to [1], in which the imaging member is replaceable.

[3] The imaging target analysis device according to [1], in which an area of a cross-section of the imaging flow channel is larger than an area of a field of view of the objective lens.

[4] A flow channel structure including
an imaging flow channel in which a fluid containing an imaging target flows in the same direction as an optical axis of an objective lens.

[5] The flow channel structure according to [4], further including
at least one fluid introduction channel that introduces the fluid into the imaging flow channel.

[6] The flow channel structure according to [5], in which a direction of the fluid introduction channel is different from a direction of the imaging flow channel.

[7] The flow channel structure according to [5] or [6], in which
at least two of the fluid introduction channels are provided, and
the at least two fluid introduction channels merge on the optical axis.

[8] The flow channel structure according to any one of [4] to [7], further including
at least one fluid ejection channel that ejects the fluid having passed through the imaging flow channel to outside of the flow channel structure.

[9] The flow channel structure according to [8], in which a direction of the fluid ejection channel is different from a direction of the imaging flow channel.

[10] The flow channel structure according to [8] or [9], in which
at least two of the fluid ejection channels are provided, and
the at least two fluid ejection channels branch from the imaging flow channel.

[11] The flow channel structure according to any one of [4] to [10], in which the fluid is a liquid.

[12] The flow channel structure according to any one of [4] to [10], in which the fluid is a liquid obtained from a living organism.

[13] The flow channel structure according to any one of [4] to [10], in which the fluid is urine or a urine-derived liquid.

[14] The flow channel structure according to any one of [4] to [13], in which the flow channel structure includes a vibrator.

[15] An imaging member including
the flow channel structure according to any one of [4] to [14].

[16] An imaging method including
imaging an imaging target in an imaging flow channel in which a fluid containing the imaging target flows in the same direction as an optical axis of an objective lens.

[17] The imaging method according to [16], in which the imaging is performed in a state in which a position of the imaging flow channel is fixed with respect to the objective lens.

[18] The imaging method according to [16] or [17], in which the imaging is performed a plurality of times.

[19] The imaging method according to [18], in which a frame rate in the imaging performed the plurality of times is not lower than a numerical value of a quotient obtained by dividing a flow velocity of the fluid in a region to which a focal point is adjusted in the imaging by a depth of field.

[20] The imaging method according to [18] or [19], further including
obtaining an image relating to a three-dimensional shape of the imaging target, on the basis of image data obtained through the imaging performed the plurality of times.

[21] An imaging target analysis system including:
an imaging member that includes a flow channel structure including an imaging flow channel in which a fluid containing an imaging target flows in the same direction as an optical axis of an objective lens; and
an imaging unit that performs imaging of the imaging target through the objective lens.

REFERENCE SIGNS LIST

100 Microscope
101 Stage
102 Objective lens
103 Stage position control device
201 Direction of flow of fluid
202 Objective lens
203 Region to which the focal point is adjusted
204 Distance as the depth of field in the optical axis direction
205, 206 Imaging target
303 Field of view
400, 600 Flow channel structure
401, 402, 601, 602 Fluid introduction channel
403, 603 Imaging flow channel
404, 405, 604, 701, 702 Fluid ejection channel
406, 606 Imaging target
407, 607 Objective lens
408 Light source
409 Illumination optical system
410, 608 Region to which the focal point is adjusted
411 Imaging optical system
412 Image sensor
413 Control unit
414 Pump
415 Flow rate sensor
416 Vibrator
800, 900 Imaging flow channel chip
801, 802, 901, 902 Fluid introduction channel
803, 903 Imaging flow channel
804, 904 Fluid ejection channel
805, 905 Region that can be observed with the objective lens of a microscope
806 Tube
906 Fluid containing imaging targets
1200 Imaging target analysis device
1201 Imaging unit
1202 Imaging member
1203 Light source unit
1204 Control unit
1205 Imaging control unit
1206 Flow rate control unit
1207 Analysis unit
1208 Image analysis unit
1209 Imaging target determining unit
1210 Imaging target counting unit
1211 Pump
1212 Flow rate sensor

The invention claimed is:

1. An imaging target analysis device comprising:
   an imaging member that includes a flow channel structure including an imaging flow channel in which a fluid containing an imaging target flows in a same direction as an optical axis of an objective lens, wherein an area of a cross-section of the imaging flow channel is larger than an area of a field of view of the objective lens; and
   an imaging unit configured to perform imaging of the imaging target through the objective lens, wherein the imaging is performed a plurality of times, and wherein a frame rate in the imaging performed the plurality of times is not lower than a numerical value of a quotient obtained by dividing a flow velocity of the fluid in a region to which a focal point is adjusted in the imaging by a depth of field.

2. The imaging target analysis device according to claim 1, wherein the imaging member is replaceable.

3. The imaging target analysis device according to claim 1, further comprising
   at least one fluid introduction channel that introduces the fluid into the imaging flow channel.

4. The imaging target analysis device according to claim 3, wherein a direction of the fluid introduction channel is different from a direction of the imaging flow channel.

5. The imaging target analysis device according to claim 3, wherein
   at least two of the fluid introduction channels are provided, and
   the at least two fluid introduction channels merge on the optical axis.

6. The imaging target analysis device according to claim 1, further comprising
   at least one fluid ejection channel that ejects the fluid having passed through the imaging flow channel to outside of the flow channel structure.

7. The imaging target analysis device according to claim 6, wherein a direction of the fluid ejection channel is different from a direction of the imaging flow channel.

8. The imaging target analysis device according to claim 6, wherein
   at least two of the fluid ejection channels are provided, and
   the at least two fluid ejection channels branch from the imaging flow channel.

9. The imaging target analysis device according to claim 1, wherein the fluid is a liquid.

10. The imaging target analysis device according to claim 1, wherein the fluid is a liquid obtained from a living organism.

11. The imaging target analysis device according to claim 1, wherein the fluid is urine or a urine-derived liquid.

12. The imaging target analysis device according to claim 1, wherein the flow channel structure includes a vibrator.

13. An imaging method comprising
    imaging an imaging target in an imaging flow channel in which a fluid containing the imaging target flows in a same direction as an optical axis of an objective lens, wherein the imaging is performed a plurality of times, and wherein a frame rate in the imaging performed the plurality of times is not lower than a numerical value of a quotient obtained by dividing a flow velocity of the fluid in a region to which a focal point is adjusted in the imaging by a depth of field.

14. The imaging method according to claim 13, wherein the imaging is performed in a state in which a position of the imaging flow channel is fixed with respect to the objective lens.

15. The imaging method according to claim 13, further comprising
    obtaining an image relating to a three-dimensional shape of the imaging target, on a basis of image data obtained through the imaging performed the plurality of times.

16. An imaging target analysis system comprising:
    an imaging member that includes a flow channel structure including an imaging flow channel in which a fluid containing an imaging target flows in a same direction as an optical axis of an objective lens, wherein an area of a cross-section of the imaging flow channel is larger than an area of a field of view of the objective lens; and
    an imaging unit that performs imaging of the imaging target through the objective lens, wherein the imaging is performed a plurality of times, and wherein a frame rate in the imaging performed the plurality of times is not lower than a numerical value of a quotient obtained by dividing a flow velocity of the fluid in a region to which a focal point is adjusted in the imaging by a depth of field.

* * * * *